United States Patent
Andreoni

(10) Patent No.: US 7,326,417 B2
(45) Date of Patent: Feb. 5, 2008

(54) IGF-1 AS FELINE VACCINE ADJUVANT, IN PARTICULAR AGAINST FELINE RETROVIRUSES

(75) Inventor: Christine Michèle Pierrette Andreoni, Villette d'Anthon (FR)

(73) Assignee: Merial Ltd., Duluth, GA (US)

( * ) Notice: Subject to any disclaimer, the term of this patent is extended or adjusted under 35 U.S.C. 154(b) by 187 days.

(21) Appl. No.: 10/238,114

(22) Filed: Sep. 10, 2002

(65) Prior Publication Data

US 2003/0100073 A1 May 29, 2003

Related U.S. Application Data

(60) Provisional application No. 60/318,686, filed on Sep. 12, 2001.

(30) Foreign Application Priority Data

Sep. 11, 2001 (FR) .................. 01 11736

(51) Int. Cl.
*A61K 39/00* (2006.01)
*C12N 15/00* (2006.01)
*C07H 21/02* (2006.01)
*C07H 21/04* (2006.01)

(52) U.S. Cl. .................. 424/184.1; 435/455; 536/23.1; 536/23.72

(58) Field of Classification Search .............. 435/5, 435/6, 325, 326, 320.1; 424/184.1, 204.1, 424/208.1; 536/23.1, 23.72
See application file for complete search history.

(56) References Cited

U.S. PATENT DOCUMENTS

| | | | |
|---|---|---|---|
| 5,202,119 A | 4/1993 | Clark et al. | |
| 5,473,054 A | 12/1995 | Jameson et al. | |
| 5,837,875 A * | 11/1998 | Bosch et al. | 800/3 |

FOREIGN PATENT DOCUMENTS

| | | |
|---|---|---|
| EP | 0 229 750 | 7/1987 |
| WO | WO 86/00619 | 1/1986 |
| WO | WO 95/16703 | 6/1995 |
| WO | WO 97/33997 | 9/1997 |
| WO | WO 98/24922 | 6/1998 |
| WO | WO 9824922 A1 * | 6/1998 |
| WO | WO 01/36483 | 5/2001 |
| WO | WO 0136483 A1 * | 5/2001 |

OTHER PUBLICATIONS

Woo, J. Investigation of Recombinant Human Insulin-Like Growth Factor Type I in Thymus Regeneration in the Acute Stage of Experimental FIV Infection. AIDS Research and Human Retroviruses 1999. vol. 15, No. 15, pp. 1377-1388.*
Josephson, N. Transduction of Feline Hematopoietic Cells by Oncoretroviral Vectors Pseudotyped with the Subgroup A Feline Leukemia Virus. Molecular Therapy Jul. 2000, vol. 2, No. 1, pp. 56-62.*
Saliki J. Canine parovirus empty capsids produced by expression in a baculovirus vector. Journal of General Virology 1992, vol. 73, pp. 369-374.*

* cited by examiner

*Primary Examiner*—Jeffrey Parkin
*Assistant Examiner*—Louise Humphrey
(74) *Attorney, Agent, or Firm*—Frommer Lawrence & Haug LLP; Thomas J. Kowalski; Angela M. Collison

(57) ABSTRACT

The invention relates to feline IGF-1, to the nucleotide sequence encoding this protein and to the use of IGF-1 as adjuvant for the vaccination of cats, in particular against the feline retroviruses FIV and FeLV. IGF-1 may be used in the form of protein or may be expressed in vivo by a suitable, e.g. viral or plasmid, expression vector. The invention relates to all types of vaccines, namely inactivated, attenuated, sub-unit and recombinant vaccines. The vectors expressing IGF-1 in vivo may also be used in immunity-stimulating compositions.

22 Claims, No Drawings

SEQUENCE LISTING

```
<160> NUMBER OF SEQ ID NOS: 20
<210> SEQ ID NO 1
<211> LENGTH: 462
<212> TYPE: DNA
<213> ORGANISM: Felis catus

<400> SEQUENCE: 1
atgggaaaaa tcagcagtct tccaacccaa ttatttaagt gctgcttttg tgatttcttg      60
aaggtaaaga tgcacatcat gtcccctct catctcttct atctgggcct gtgcttgctc     120
accttcacca gctctgccac agctggacca gagacgctct gtggggctga gttggtggac     180
gctcttcagt tcgtgtgtgg agacaggggt ttttatttca acaagcccac ggggtatggc     240
tccagcagtc ggagggcacc tcagacaggc atcgtggatg agtgctgctt ccggagctgt     300
gatctgaggc ggctagagat gtactgtgca ccctcaagc ctgccaagtc tgcccgctca     360
gtccgtgctc agcgccacac tgacatgccc aaggctcaga aggaagtaca tttgaagaac     420
gcaagtagag ggagtgcggg aaacaagaac tacagaatgt ag                        462

<210> SEQ ID NO 2
<211> LENGTH: 153
<212> TYPE: PRT
<213> ORGANISM: Felis catus

<400> SEQUENCE: 2
```

```
Met Gly Lys Ile Ser Ser Leu Pro Thr Gln Leu Phe Lys Cys Cys Phe
1               5                   10                  15

Cys Asp Phe Leu Lys Val Lys Met His Ile Met Ser Pro Ser His Leu
            20                  25                  30

Phe Tyr Leu Gly Leu Cys Leu Leu Thr Phe Thr Ser Ser Ala Thr Ala
                35                  40                  45

Gly Pro Glu Thr Leu Cys Gly Ala Glu Leu Val Asp Ala Leu Gln Phe
        50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
                100                 105                 110

Lys Pro Ala Lys Ser Ala Arg Ser Val Arg Ala Gln Arg His Thr Asp
                115                 120                 125

Met Pro Lys Ala Gln Lys Glu Val His Leu Lys Asn Ala Ser Arg Gly
        130                 135                 140

Ser Ala Gly Asn Lys Asn Tyr Arg Met
145                 150
```

```
<210> SEQ ID NO 3
<211> LENGTH: 105
<212> TYPE: PRT
<213> ORGANISM: Felis catus

<400> SEQUENCE: 3
```

```
Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
                35                  40                  45

Phe Arg Ser Cys Asp Leu Arg Arg Leu Glu Met Tyr Cys Ala Pro Leu
        50                  55                  60

Lys Pro Ala Lys Ser Ala Arg Ser Val Arg Ala Gln Arg His Thr Asp
65                  70                  75                  80

Met Pro Lys Ala Gln Lys Glu Val His Leu Lys Asn Ala Ser Arg Gly
                85                  90                  95

Ser Ala Gly Asn Lys Asn Tyr Arg Met
                100                 105
```

```
<210> SEQ ID NO 4
<211> LENGTH: 39
<212> TYPE: DNA
<213> ORGANISM: Unknown
<220> FEATURE:
<223> OTHER INFORMATION: EL490 oligonucleotide used in reverse
      transcription

<400> SEQUENCE: 4
acgccgtcga catgggaaaa atcagcagtc ttccaaccc                          39

<210> SEQ ID NO 5
<211> LENGTH: 42
<212> TYPE: DNA
<213> ORGANISM: Unknown
<220> FEATURE:
```

```
<223> OTHER INFORMATION: FC124 oligonucleotide used in reverse
      transcription

<400> SEQUENCE: 5
cgcggatccc tacattctgt agttcttgtt tcccgcactc cc                    42

<210> SEQ ID NO 6
<211> LENGTH: 36
<212> TYPE: DNA
<213> ORGANISM: Unknown
<220> FEATURE:
<223> OTHER INFORMATION: FC116 oligonucleotide used in reverse
      transcription

<400> SEQUENCE: 6 tttttctgc agcaataaga atggcagaag gatttg                             36

<210> SEQ ID NO 7
<211> LENGTH: 36
<212> TYPE: DNA
<213> ORGANISM: Unknown
<220> FEATURE:
<223> OTHER INFORMATION: FC117 oligonucleotide used in reverse
      transcription

<400> SEQUENCE: 7
tcgcacctga aacatctcga gtgtttccac atgtat                            36

<210> SEQ ID NO 8
<211> LENGTH: 36
<212> TYPE: DNA
<213> ORGANISM: Unknown
<220> FEATURE:
<223> OTHER INFORMATION: FC118 oligonucleotide used in reverse
      transcription

<400> SEQUENCE: 8
atacatgtgg aaacactcga gatgtttcag gtgcga                            36

<210> SEQ ID NO 9
<211> LENGTH: 54
<212> TYPE: DNA
<213> ORGANISM: Unknown
<220> FEATURE:
<223> OTHER INFORMATION: FC119 oligonucleotide used in reverse
      transcription

<400> SEQUENCE: 9 tttttttggat ccccgggct gcaggaattc tgagatactt catcattcct cctc        54

<210> SEQ ID NO 10
<211> LENGTH: 37
<212> TYPE: DNA
<213> ORGANISM: Unknown
<220> FEATURE:
<223> OTHER INFORMATION: BP670 oligonucleotide used in reverse
      transcription

<400> SEQUENCE: 10
tttgtcgaca aggtaggaga gattctacag caacatg                           37

<210> SEQ ID NO 11
<211> LENGTH: 40
<212> TYPE: DNA
<213> ORGANISM: Unknown
<220> FEATURE:
<223> OTHER INFORMATION: BP674 oligonucleotide used in reverse
``` transcription

<400> SEQUENCE: 11
tttgcggccg cgttattgag ccattactaa cctaatattg                    40

<210> SEQ ID NO 12
<211> LENGTH: 48
<212> TYPE: DNA
<213> ORGANISM: Unknown
<220> FEATURE:
<223> OTHER INFORMATION: FC120 oligonucleotide used in reverse
      transcription

<400> SEQUENCE: 12
tttttacctg catttccttc ttccagtttt acctcttgaa tttcgttc           48

<210> SEQ ID NO 13
<211> LENGTH: 48
<212> TYPE: DNA
<213> ORGANISM: Unknown
<220> FEATURE:
<223> OTHER INFORMATION: BP672 oligonucleotide used in reverse
      transcription

<400> SEQUENCE: 13
tttactggaa gaaggaaatg caggtaaaag gaaaagacaa agaagaag           48

<210> SEQ ID NO 14
<211> LENGTH: 36
<212> TYPE: DNA
<213> ORGANISM: Unknown
<220> FEATURE:
<223> OTHER INFORMATION: BP673 oligonucleotide used in reverse
      transcription

<400> SEQUENCE: 14
tttagatctt tagtccataa gcattctttc tatttc                       36

<210> SEQ ID NO 15
<211> LENGTH: 29
<212> TYPE: DNA
<213> ORGANISM: Unknown
<220> FEATURE:
<223> OTHER INFORMATION: BP680 oligonucleotide used in reverse
      transcription

<400> SEQUENCE: 15
tttctgcaga tggaagacat aatagtatt                               29

<210> SEQ ID NO 16
<211> LENGTH: 32
<212> TYPE: DNA
<213> ORGANISM: Unknown
<220> FEATURE:
<223> OTHER INFORMATION: BP681 oligonucleotide used in reverse
      transcription

<400> SEQUENCE: 16
tttagatctc taagcagtag ttattgataa tg                           32

<210> SEQ ID NO 17
<211> LENGTH: 29
<212> TYPE: DNA
<213> ORGANISM: Unknown
<220> FEATURE:
<223> OTHER INFORMATION: BP247 oligonucleotide used in reverse
      transcription

```
<400> SEQUENCE: 17
tttgtcgacc atggaaagtc caacgcacc                                          29

<210> SEQ ID NO 18
<211> LENGTH: 28
<212> TYPE: DNA
<213> ORGANISM: Unknown
<220> FEATURE:
<223> OTHER INFORMATION: BP249 oligonucleotide used in reverse
      transcription

<400> SEQUENCE: 18
tttggatcct catggtcggt ccggatcg                                           28

<210> SEQ ID NO 19
<211> LENGTH: 33
<212> TYPE: DNA
<213> ORGANISM: Unknown
<220> FEATURE:
<223> OTHER INFORMATION: BP283 oligonucleotide used in reverse
      transcription

<400> SEQUENCE: 19
ttgtcgacat gtctggagcc tctagtggga cag                                     33

<210> SEQ ID NO 20
<211> LENGTH: 40
<212> TYPE: DNA
<213> ORGANISM: Unknown
<220> FEATURE:
<223> OTHER INFORMATION: BP284 oligonucleotide used in reverse
      transcription

<400> SEQUENCE: 20 ttggatccttt atttaattac tgcagttcca aggaactctc                             40
```

US 7,326,417 B2

IGF-1 AS FELINE VACCINE ADJUVANT, IN PARTICULAR AGAINST FELINE RETROVIRUSES

RELATED APPLICATIONS

This application claims priority from French Patent Application 01 11736 filed Sep. 11, 2001 and U.S. Provisional application Ser. No. 60/318,686, filed Sep. 12, 2001.

FIELD OF THE INVENTION

The present invention relates to the feline growth factor IGF-1, to a polynucleotide encoding this IGF-1 and to expression vectors containing it. The invention also relates to the use of IGF-1 as vaccine adjuvant for the feline species, in particular for vaccines against feline retroviruses.

Each document cited in this text (*application cited documents*) and each document cited or referenced in each of the application cited documents, is hereby incorporated herein by reference; and, technology in each of the documents incorporated herein by reference can be used in the practice of this invention.

BACKGROUND OF THE INVENTION

IGF-1 is an endocrine growth mediator. It is the main effector of the growth hormone. IGF-1 also plays a part in the complex system of regulation of immunity and of inflammation on the sides of cytokines, of hormones (in particular cortisol, the growth hormone).

U.S. Pat. No. 5,202,119 describes the therapeutic use of human IGF-1 as an immunity stimulant in man and, more particularly, in immunodeficient individuals. A particular application is the combination of human IGF-1 with an immunogen to stimulate the production of antibodies to this immunogen. This patent aims to extend the application to mammals in general and to the avian species, but without describing animal IGF-1 sequences or providing the results of experiments on animals.

The Applicant has found that IGF-1 stimulates more particularly the cellular response in general. This response profile has turned out to be particularly well adapted in the case of feline retroviruses. It also stimulates mucosal immunity.

Until the invention, moreover, the gene encoding feline IGF-1 was not available.

DESCRIPTION OF THE INVENTION

The Applicant has succeeded in isolating and sequencing the IGF-1 gene originating from cats' peripheral blood mononuclear cells (BPMC). This gene was isolated after a polymerase chain reaction (PCR) using the oligonucleotides described in the examples.

The feline IGF-1 gene has a size of 462 nucleotides (SEQ ID NO: 1) and codes for a protein containing 153 amino acids (SEQ ID NO: 2). At the N-terminal of the protein as defined in SEQ ID NO: 2 there is a signal peptide sequence of 48 amino acids (from 1 to 48 in the sequence SEQ ID NO: 2) serving for the secretion of the protein, this signal peptide being cleaved secondarily. The mature protein (SEQ ID NO: 3) of 105 amino acids corresponds to the amino acids 49 to 153 of SEQ ID NO: 2.

The present invention relates to the DNA sequence encoding feline IGF-1 and its complementary strand and to the corresponding RNA sequence, and to the equivalent sequences obtained by degeneracy of the genetic code.

A first object of the invention is therefore an isolated polynucleotide (DNA, in particular cDNA, or RNA, by definition) comprising nucleotide sequence SEQ ID NO: 1 or the same sequence with substitution of the T by U to form the RNA sequence. A further subject is the isolated polynucleotide having this sequence. The present invention also relates to an isolated polynucleotide encoding amino acid sequence SEQ ID NO: 2 or 3.

By definition, the notion of IGF-1 according to the invention covers the IGF-1 of feline origin and the proteins having identity equal to or higher than 98.5% and preferably 99% with SEQ ID NO: 2. The polynucleotides coding for these proteins of feline origin or the homologues thus defined form part of the invention.

Thus the invention relates to a polynucleotide encoding a polypeptide or protein having the function of feline IGF-1, selected from the group comprising:
  (a) A polynucleotide comprising or consisting essentially of nucleotide sequence as depicted in SEQ ID NO: 1 or its complementary strand
  (b) A polynucleotide encoding a polypeptide having the amino acid sequence as depicted in SEQ ID NO: 2 or 3
  (c) A polynucleotide the sequence of which differs from the sequence of (a) due to the replacement of T by U.

By way of equivalence, this includes a polynucleotide encoding a polypeptide or protein having the function of feline IGF-1, such as:
  (d) A polynucleotide the sequence of which differs from the sequence of (a) or (b) due to the degeneracy of the genetic code
  (e) A polynucleotide encoding a polypeptide having identity equal to or higher than 98.5% and preferably than 99% with SEQ ID NO: 2.

The percentage of identity is determined using the Basic Local Alignment Search Tool (BLAST) (Altschul et al., *J. Mol. Biol.* 215:403, 1990), this program is available from several sources, including the National Center for Biotechnology Information (NCBI, Bethesda, Md.) and on the Internet. The comparison between the sequences is made over the full length alignment with the amino acid sequence given in this present disclosure, employing the NCBI Blast 2 sequences function using the blastp default BLOSUM62 matrix set to default parameters (gap existence cost of 11, and a per residue gap cost of 1).

The polynucleotides according to the invention may be obtained by chemical synthesis or by expression using appropriate expression vectors.

The present invention also relates to the feline IGF-1 proteins or polypeptides isolated or produced in mature forms or their precursors. The invention therefore relates, in particular, to:
  (f) a polypeptide comprising or consisting essentially of SEQ ID NO: 2 or SEQ ID NO: 3,
  (g) a polypeptide encoded by SEQ ID NO: 1 or by any one of polynucleotides (a) to (c) above.

By way of equivalence, this includes a protein or polypeptide having the function of IGF-1, wherein the polypeptide has identity equal to or higher than 98.5% and preferably than 99% with SEQ ID NO: 2.

The IGF-1 protein or polypeptide may be expressed and isolated in mature form in a system of cells allowing the secretion thereof and the cleavage of the signal peptide at 5'. It may also be expressed and isolated in precursor form.

The present invention also relates to the expression vectors containing a polynucleotide as defined above as an insert, and the elements allowing expression of the polynucleotide.

The nucleotide sequence may be inserted into conventional in vitro expression vectors, in particular of viral origin such as *Baculovirus* or of plasmid origin. These vectors are then used to infect or transfect appropriate systems of cells such as insect cells, cells of prokaryotic origin (for example *Escherichia coli*) or eukaryotic origin, in particular yeasts, in particular *Saccharomyces cerevisiae*, mammalian cells, in particular hamster cells (for example CHO cells) and cat cells (for example CRFK cells). It is preferable to use the *Baculovirus* (U.S. Pat. No. 4,745,051; Vialard J. et al., J. Virol., 1990, 64(1), 37-50; Verne A., Virology, 1988, 167, 56-71) e.g. Autographa californica Nuclear Polyhedrosis Virus AcNPV as vector to express the IGF-1 in insect cells, in particular cells of *Spodoptera frugiperda* Sf9 (ATCC CRL 1711 deposit). A person skilled in the art is familiar with and able to use the methods of producing proteins adapted to the selected system and thus obtain and isolate the IGF-1 protein. The invention therefore also covers these in vitro expression vectors comprising a polynucleotide according to the invention and the elements allowing expression thereof in the host cells, the feline IGF-1 protein thus produced and its use as vaccine adjuvant and non-specific immunity stimulant.

Preferably, the polynucleotide according to the invention is introduced into in vivo expression vectors under conditions allowing the expression of a functional polypeptide or feline IGF-1 protein in the host. These expression vectors may be plasmids, viral vectors such as poxviruses, for example attenuated mutants of the vaccinia virus, avipox (in particular canarypox, fowlpox), swinepox, raccoonpox, adenoviruses (in particular CAV-2) and herpes viruses such as the feline herpes virus FHV. Of the viral vectors, canarypox and FHV are preferred. These vectors comprise the elements allowing the expression of the polynucleotide in the host.

With regard to the poxviruses, a person skilled in the art can refer to WO-A-90/12882 and, more particularly, with regard to the vaccinia virus to U.S. Pat. Nos. 4,769,330; 4,722,848; 4,603,112; 5,110,587; 5,494,807, 5,762,938; with regard to fowlpox to U.S. Pat. Nos. 5,174,993; 5,505,941; 5,766,599; and with regard to canarypox to U.S. Pat. No. 5,756,103.

As attenuated mutant of vaccinia virus, one may mention the MVA (Ankara strain) (Stickl H. and Hochstein-Mintzel V., Munch, Med. Wschr., 1971, 113, 1149-1153; Sutter G. et al., Proc. Natl. Acad. Sci. USA., 1992, 89, 10847-10851; commercial strain ATCC VR-1508; MVA is obtained after 570 passages of the Ankara vaccinia strain on chicken embryo fibroblasts), or the NYVAC (its construction is described in U.S. Pat. No. 5,494,807, in particular in examples 1 to 6; this patent also describes insertion of heterologous genes within insertion sites in this recombinant, and the use of appropriate promoters; see also WO-A-96/40241).

According to one of the preferred embodiments of the invention, the poxvirus expression vector is a canarypox virus, optionally attenuated, e.g. an ALVAC or a canarypox virus (for example of the Rentschler strain) which has been attenuated, in particular by more than 200 passages on chick embryo fibroblast (CEF) cells. An ALVAC strain canarypox virus was registered, on Nov. 14, 1996, with the American Type Culture Collection (ATCC) under the accession number VR-2547. A canarypox is commercially available at the ATCC under reference VR-111. Attenuated canarypox viruses are described in U.S. Pat. No. 5,756,103 and WO-A-01/05934.

Other attenuated poxviruses may be used, in particular attenuated fowlpoxes (e.g. TROVAC). Regarding the TROVAC poxvirus, those skilled in the art may refer to patent WO-A-96/40241. A number of fowlpox vaccinal strains are available, e.g. the vaccine DIFTOSEC CT® sold by Merial and the vaccine NOBILIS® sold by Intervet.

If the expression vector is an attenuated mutant of the vaccinia virus, the insertion sites of the polynucleotide(s) to be expressed are, in particular, the thymidine kinase (TK) gene, the hemagglutinin (HA) gene and the region of the type A inclusion bodies (ATI). Insertion of genes in the MVA virus is also described in several publications, e.g. in M. W. Carroll et al., Vaccine 1997, 15(4), 387-394; K. J. Stittelaar et al., J. Virol. 2000, 74(9), 4236-4243; G. Sutter et al., Vaccine 1994, 12(11), 1032-1040, to which the one skilled in the art may refer. The complete genome of MVA is described in G. Antoine, Virology 1998, 244, 365-396, which allows one to find other insertion sites and other promoters.

In the case of canarypox, the insertion sites are, in particular, located in or formed by the open reading frames (ORFs) C3, C5 and C6. In the case of fowlpox, the insertion sites are, in particular, located in or formed by the ORFs F7 and F8.

Preferably, if the expression vector is a poxvirus, the polynucleotide to be expressed is inserted under the control of a poxvirus specific promoter, in particular the vaccinia 7.5 kDa promoter (Cochran et al., J. Virology, 1985, 54, 30-35), the vaccinia I3L promoter (Riviere et al., J. Virology, 1992, 66, 3424-3434), the vaccinia HA promoter (Shida, Virology, 1986, 150, 451-457), the cowpox ATI promoter (Funahashi et al., J. Gen. Virol., 1988, 69, 35-47), or else the vaccinia H6promoter (Taylor J. et al., Vaccine, 1988, 6, 504-508; Guo P. et al., J. Virol., 1989, 63, 4189-4198; Perkus M. et al., J. Virol., 1989, 63, 3829-3836).

If the expression vector is a FHV, the sites of insertion of the polynucleotide(s) to be expressed are, in particular, the open reading frames (ORFs) ORF2 and ORF5 (U.S. Pat. No. 6,074,649).

Preferably, if the expression vector is a herpes virus, the polynucleotide to be expressed is inserted under the dependency of signals regulating the transcription and in particular of promoters, preferably brought by the insertion, for example the early promoter of the cytomegalovirus or CMV-IE (Cytomegalovirus Immediate Early), in particular of human origin (hCMV-IE), from rats, guinea pigs or preferably of murine origin (mCMV IE), the early and late promoters of the virus SV40 (Simian Virus 40), the late promoters of glycoproteins, in particular of gB, gC and gD, of alpha herpes viruses, in particular of feline herpes viruses (FHV).

By definition, a plasmid comprises at least one transcription unit comprising a polynucleotide of interest, for example the one encoding IGF-1 and the elements required for the in vivo expression thereof. The circular, super-coiled or otherwise, plasmid form is preferred. The linearised form also falls within the scope of this invention.

Each plasmid comprises a promoter capable of ensuring, in host cells, the expression of the polynucleotide inserted under its control. It is, in general, a strong eukaryotic promoter. The cytomegalovirus immediate early (CMV-IE) promoter, of human or murine origin, or optionally of any other origin such as rat or guinea pig, is the preferred strong eukaryotic promoter. The CMV-IE promoter may comprise the actual promoter component, which may or may not be associated with the enhancer component. Reference may be made to EP-A-260 148, EP-A-323 597, U.S. Pat. Nos. 5,168,062, 5,385,839, 4,968,615 and WO-A-87/03905. Human (Boshart M. et al., Cell., 1985, 41, 521-530) or murine CMV-IE is preferred.

More generally, the promoter is either of viral origin or of cellular origin. As a strong viral promoter other than CMV-IE, mention may be made of the early promoter or the late promoter of the virus SV40, or the LTR promoter of the Rous sarcoma virus. As a strong cellular promoters, mention may be made of the cytoskeleton gene promoter, such as, the desmin promoter (Kwissa M. et al., Vaccine, 2000, 18(22), 2337-2344) or else the actin promoter (Miyazaki J. et al., Gene, 1989, 79(2), 269-277).

If several genes are present in the same plasmid, they may be presented in the same transcription unit or in several different units.

By equivalence, the sub-fragments of these promoters, maintaining adequate promoter activity, are included in the present invention: e.g. the truncated CMV-IE promoters according to WO-A-98/00166. The notion of promoter according to the invention therefore includes the derivatives and sub-fragments maintaining adequate promoter activity, preferably substantially similar to that of the proper promoter from which they are derived. With regard to CMV-IE, this notion includes the proper promoter part and/or the enhancer part and the derivatives and sub-fragments.

The expression vectors can also incorporate other transcription-regulating elements such as stabilizing sequences of the intron type, e.g. intron II of the rabbit beta-globin gene (van Ooyen et al. Science, 1979, 206: 337-344) and/or a signal sequence, e.g. of the human tissue plasminogen activator gene (tPA; Montgomery et al., Cell. Mol. Biol. 1997, 43; 285-292), and/or a polyadenylation signal (polyA), e.g. of the gene of the bovine growth hormone (bGH) (U.S. Pat. No. 5,122,458) or of the rabbit beta-globin gene, or that of the SV40 virus. For instance, the signal sequence of the IGF-1 may be replaced by a signal sequence of another origin.

According to the invention, feline IGF-1 may be used as vaccine adjuvant, in particular to increase the cellular and/or mucosal immune response directed against one or more feline immunogens, in particular feline retrovirus immunogens such as immunogens from the feline immunodeficiency virus (FIV) and feline leukaemia virus (FeLV). IGF-1 from other species may also be used for this purpose, but feline IGF-1 is preferred.

The invention therefore relates to the compositions intended to induce an immune response against a feline pathogen in a member of the *feline* species, in particular a cat. The immunogenic or vaccine compositions according to the invention comprise an IGF-1 protein or polypeptide, preferably feline IGF-1 according to the invention or a recombinant vector expressing this protein or polypeptide in vivo, at least one feline immunogen or a recombinant vector expressing such an immunogen in vivo, in particular at least one FIV and/or FeLV immunogen or a recombinant vector expressing this immunogen in vivo, and an excipient or vehicle which is acceptable for veterinary use. The notion of immunogenic composition includes any preparation capable of inducing an immune response directed against the pathogen under review, once administered to the feline, in particular to the cat, this response being increased by the presence of the IGF-1 protein. It is preferably a vaccine composition capable of inducing effective protection or a certain degree of protection against this pathogen, this degree of protection being increased by the presence in vivo of the IGF-1 protein or polypeptide, in particular feline IGF-1.

The immunogenic and vaccine compositions targeted in the invention include all known types, namely inactivated compositions, attenuated live compositions, sub-units and recombinant vectors. Thus unless indicated otherwise herein, the word immunogen encompasses an inactivated microorganism, a live attenuated microorganism, one or several microorganism subunits, or combinations thereof. The term immunogen expressed by a vector denotes in particular a peptide, polypeptide or protein capable of inducing an immune response against a pathogenic agent in the host; it may be an entire protein or glycoprotein or an immunologically active fragment thereof.

As seen hereinbefore, the IGF-1 protein or polypeptide may be added as it is to the immunogen to form, in the presence of an excipient or vehicle which is acceptable for veterinary use, a ready-to-administer composition. The IGF-1 protein may also be combined with a slow release system intended to release the protein gradually. In the immunogenic composition or vaccine, the IGF-1 protein or polypeptide can be:
  i. a polypeptide as defined under (f) or (g)
  ii. a polypeptide comprising or consisting essentially of amino acids 49-118 on SEQ ID NO: 2
  iii. a polypeptide having identity equal to or higher than 70%, in particular equal to or higher than 75, 80, 85, 90 or 95%, more particularly 98.5% and preferably 99% with a polypeptide according to i or ii.

The word polypeptide includes by way of equivalence the fragments thereof which keep substantially the adjuvant power of the IGF-1, e.g. of the mature feline IGF-1 (which in the application is exemplified by amino acid sequence 49-153 or its fragment 49-118).

According to a particular feature of the invention, the IGF-1 protein may be expressed in vivo using an in vivo expression vector or recombinant vector as described hereinbefore. In this case, it is also preferable to have the feline immunogen expressed by means of a recombinant vector of the same type as or of a different type from the one expressing the IGF-1 protein. A same in vivo expression vector, comprising and expressing at least one immunogen and the IGF-1 protein may also be used. The in vivo expression vector can comprise:
  1. a polynucleotide as defined under (a) to (c) and its equivalents.
  2. a polynucleotide encoding a polypeptide having identity equal to or higher than 70%, in particular equal to or higher than 75, 80, 85, 90 or 95%, more particularly than 98.5% and preferably than 99% with SEQ ID NO: 2.
  3. a polynucleotide encoding a polypeptide comprising or consisting essentially of amino acids 49-118 on SEQ ID NO: 2.

Therefore, the present invention preferably relates to immunogenic compositions or vaccines comprising:
  an in vivo expression vector containing a polynucleotide encoding a preferably feline IGF-1 under conditions allowing expression of a functional IGF-1 protein in the feline, in particular in the cat,
  at least one in vivo expression vector containing at least one polynucleotide encoding a FIV and/or FeLV immunogen, wherein this vector may also be the one expressing IGF-1, and
  a vehicle or excipient which is acceptable for veterinary use.

For the subunit vaccines and the recombinant vaccines, the immunogens are preferably, with regard to the FeLV virus, the envelope (env) glycoprotein or the gag/pol protein or the combinations of these FeLV immunogens and, with regard to FIV, the env, gag/pro, rev or tat proteins or combinations thereof, preferably env and gag, optionally combined with rev and/or tat. With regard to the recombinant vaccines, a nucleotide sequence encoding the immunogen under review is inserted into the expression vector under dependency of the signals required for its in vivo expression.

The advantages of using IGF-1 for vaccinations are, in particular, the increase in the cellular and mucosal responses and the reduction in the dose of immunogen or recombinant vector used. Furthermore, in certain animals which do not respond after administration of conventional vaccine, the use of IGF-1 in combination with the conventional vaccine stimulates the immune response and its increase to a protective level.

An advantageous feature of the invention is the use of a vector for in vivo expression of IGF-1 which increases the period of action of IGF-1. It is preferable to use an in vivo expression vector for IGF-1, whatever the form of the immunogen.

According to a particular feature, the invention covers compositions comprising a plasmid encoding and expressing preferably feline IGF-1 or polypeptide according to the invention and at least one further plasmid encoding and expressing at least one feline immunogen.

Examples of plasmid constructions containing feline immunogens useful in the invention are given in WO-A-98/03660. As embodiments, the present invention provides for the use of plasmids as disclosed in WO-A-98/03660, in particular those described in examples 7-9 (expressing FeLV immunogens env, gag/pol) and 17-18 (expressing FIV immunogens env, gag/pro) of WO-A-98/03660. And for instance, the invention provides for the combination of a plasmid expressing a preferably feline IGF-1 or polypeptide and of one or several of the plasmids as disclosed in WO-A-98/03660. The invention also covers compositions comprising a plasmid simultaneously encoding and expressing preferably feline IGF-1 or polypeptide according to the invention and at least one FeLV or FIV immunogen. And thus the present invention may use plasmids as disclosed in these examples of WO-A-98/03660, wherein a polynucleotide according to the invention has been further inserted.

The invention also applies to immunization against feline pathogens other than FIV and FeLV. As other pathogens, mention may be made in particular to feline panleukopenia virus (FPV), feline infectious peritonitis virus (FIPV), feline herpes virus (FHV), feline calicivirus (FCV), rabies virus and *Chlamydia*. As shown hereinbefore, the vaccines may be attenuated vaccines, inactivated vaccines, subunit vaccines or recombinant vaccines. In the case of subunit vaccines and recombinant vaccines, the feline immunogens are preferably selected from the capsid protein VP2 for FPV, the glycoproteins S, M, N and combinations thereof for FIPV, the glycoproteins gB, gC, gD and combinations thereof for FHV, the capsid protein C for FCV and the glycoprotein G for the rabies virus.

For example, one may use the plasmids described in WO-A-98/03660 (FPV VP2 gene in example 10, FIPV S, M, N in examples 11-13, FHV gB, gD genes in examples 14-15, FCV C gene in example 16, rabies G gene in example 19) and WO-A-00/77043 (FHV gB, gC, gD genes in example 5). Thus the invention comprehends compositions combining such plasmid(s) and a plasmid encoding preferably feline IGF-1 protein or polypeptide. The invention also comprehends compositions comprising a plasmid simultaneously encoding and expressing preferably feline IGF-1 or polypeptide according to the invention and at least one feline immunogen. And thus the present invention may use plasmids as disclosed in these examples of WO-A-98/03660 and WO-A-00/77043, wherein a polynucleotide according to the invention has been further inserted. And the above description of plasmids and viral vectors, e.g. poxviruses, will also apply to these other feline pathogens.

As other embodiments of the invention, the plasmids exemplified in WO-A-98/03660 and WO-A-00/77043 may also be combined with an IGF-1 or polypeptide according to the invention, under protein form.

This invention also covers compositions in which the immunogenic or vaccine preparation comprises immunogens from two or more of these pathogens and, more particularly, immunogen(s) from one or more of these pathogens and immunogen(s) from FIV and/or FeLV.

The compositions according to the invention may also comprise one or more further immunity adjuvants selected, in particular, from those conventionally used in feline vaccination for the vaccine(s) under consideration. Conventional compositions (inactivated vaccines, attenuated live vaccines, subunit vaccines) may thus comprise, as conventional adjuvant, compounds of the carbomer type, aluminium hydroxide, or may be formulated in the form of an oil-in-water or water-in-oil-in-water emulsion. In the case of the compositions based on viral expression vector, compounds of the carbomer type and oil-in-water or water-in-oil-in-water emulsions may be cited.

The plasmid compositions may advantageously be formulated with a cationic lipid containing a quaternary ammonium salt. These lipids are preferably those corresponding to the following formula:

$$R_1-O-CH_2-CH-CH_2-N^+-R_2-X$$
$$\phantom{R_1-O-CH_2-}|\phantom{CH-CH_2-}|$$
$$\phantom{R_1-O-CH_2-}OR_1\phantom{-CH_2-}CH_3$$

with $CH_3$ on the nitrogen.

in which $R_1$ is a saturated or unsaturated linear aliphatic radical containing 12 to 18 carbon atoms, $R_2$ is a further aliphatic radical containing 2 or 3 carbon atoms and X is a hydroxyl or amine group.

Preferred cationic lipids include DMRIE (N-(2-hydroxyethyl)-N,N-dimethyl-2,3-bis(tetradecyloxy)-1-propane ammonium; WO-A-96/34109), preferably combined with a neutral lipid, preferably DOPE (dioleoyl-phosphatidyl-ethanolamine; Behr J. P., 1994, Bioconjugate Chemistry, 5, 382-389), to form DMRIE-DOPE.

Preferably, a mixture of plasmid with this adjuvant is formed extemporaneously and it is preferable to give the mixture formed in this way time to complex, for example for a period of 10 to 60 minutes, in particular of about 30 minutes, prior to administration thereof.

If DOPE is present, the molar ratio DMRIE:DOPE will preferably be 95:5 to 5:95, more particularly 1:1.

The ratio by weight of plasmid:adjuvant DMRIE or DMRIE-DOPE can range, in particular, from 50:1 to 1:10, in particular from 10:1 to 1:5, and preferably from 1:1 to 1:2.

The present invention also relates to methods of immunization and of vaccination of felines, in particular cats, in particular against the feline retroviruses FIV and FeLV.

These methods involve the administration of an effective amount of an immunogenic composition or of a vaccine according to the invention. This administration may be made, in particular, parenterally, e.g. by subcutaneous, intradermal or intramuscular administration, or by oral and/or nasal routes.

These methods may be intended, in particular, to increase the cellular and/or mucosal immune response to the associated immunogen(s), in particular to FIV and/or FeLV.

The present invention also relates to non-specific immunity-stimulating compositions, in other words compositions based on an IGF-1 protein or polypeptide according to the invention which are be used as general immunity stimulant. The invention also concerns a method for stimulating immunity comprising the administration of the composition. These compositions are administered in the presence or in the absence of declared pathology, generally independently of a vaccine, in order to reinforce immunity, in particular of a feline, preferably of a cat. These compositions preferably comprise viral or plasmid recombinant vectors which express in vivo an IGF-1 protein or polypeptide according to the invention and an excipient or vehicle which is acceptable for veterinary use, these compositions allowing long-term production of IGF-1 in the organism. The characteristics of the vectors, polypeptides and polypeptides are as defined above. These compositions can also comprise one or more adjuvants as described hereinbefore.

The various compositions and vaccines may be injected using a needleless liquid jet injector.

The immunogenic compositions and vaccines according to the invention comprise an effective amount of plasmid or viral vector, a person skilled in the art being able of determining these amounts. The Applicant recommends:

in the case of immunogenic compositions or vaccines based on plasmid, a dose may contain from about 1 µg to about 2,000 µg, in particular from about 50 µg to about 1,000 µg. The volume of dose may be between 0.1 and 2 ml, preferably between 0.2 and 1 ml.

in the case of the immunogenic compositions or the vaccines based on a viral vector, e.g. a poxvirus, a dose may be between about $10^3$ pfu and about $10^9$ pfu. If the vector is the canarypox virus, the dose is more particularly between about $10^5$ pfu and about $10^9$ pfu, preferably between about $10^6$ pfu and about $10^8$ pfu. If the vector is the feline herpes virus, the dose is more particularly between about $10^2$ $CCID_{50}$ and about $10^7$ $CCID_{50}$. The volumes of dose of the immunogenic compositions and of the feline vaccines based on viral vectors are generally between 0.1 and 2.0 ml, preferably between 0.2 and 1.0 ml.

If the IGF-1 protein or polypeptide is brought in protein form, the dose may be from 20 to 2,000 µg and preferably from 100 to 500 µg.

The present invention is additionally described by the following illustrative, non-limiting examples.

EXAMPLES

All the plasmid constructions were produced using standard molecular biology techniques (digestion by restriction enzymes, synthesis of a single strand complementary DNA, polymerase chain reaction, elongation of an oligonucleotide by a polymerase DNA, etc.) described by Sambrook J. et al. (*Molecular Cloning: A Laboratory Manual*, 2nd Edition, Cold Spring Harbor Laboratory, Cold Spring Harbor, N.Y., 1989). All restriction fragments used for the present invention as well as the various polymerase chain reaction (PCR) fragments were isolated and purified using the Geneclean® kit (BIO101 Inc. La Jolla, Calif.).

Example 1

Preparation of Total RNA From Cat Lymphocytes

Some cat's blood was collected on a heparinised tube by taking blood from the jugular vein. In the absence of stimulation, the mononuclear cells were collected by centrifugation on a Ficoll gradient. The total RNA of these cells contained in 100 ml of suspension was extracted using the High pure RNA isolation kit (Roche Molecular Biochemicals, Cat #1 828 665), following the supplier's instructions for the extraction stages. The RNA sediment obtained at the end of extraction was resuspended with 1 to 2 ml of sterile distilled water without RNase.

Example 2

Isolation of the Gene Encoding Feline IGF-1

The complementary DNA (cDNA) of feline IGF-1 is synthesized with the Gene Amp RNA PCR Kit (Cat #N 808 0017, Perkin-Elmer, Norwalk, Conn. 06859, USA), using the conditions provided by the supplier.

A reverse transcription reaction followed by a polymerase chain reaction (RT-PCR) was carried out with 50 µl of the feline RNA suspension (example 1), the polymerase Pfu (Stratagene, Cat #600154) and with the following oligonucleotides:

```
EL490 (39 mer)
                                        (SEQ ID NO:4)
5'ACGCCGTCGACATGGGAAAAATCAGCAGTCTTCCAACCC3' and FC124 (42 mer)
                                        (SEQ ID NO:5)
5'CGCGGATCCCTACATTCTGTAGTTCTTGTTTCCCGCACTCCC3'
```

This pair of oligonucleotides allows the incorporation of a SalI restriction site, a BamHI restriction site, an ATG initiation codon at 5' of the insert and a stop codon at 3' of the insert.

The synthesis of the first cDNA strand takes place by elongation of the hexamer of the kit after hybridization of the latter with the RNA matrix.

The synthesis conditions of the first cDNA strand are a temperature of 42° C. for 20 min, then 99° C. for 5 min and finally 4° C. for 5 min. The conditions of the PCR reaction in the presence of the pair of oligonucleotides EL490 and FC124 are a temperature of 95° C. for 2 min then 40 cycles (95° C. for 30 sec, then 55° C. for 45 sec, and 72° C. for 1 min) and finally 72° C. for 10 min in the presence of the Taq DNA polymerase (Gibco BRL, Cleveland, Ohio, USA, Cat #18038-26) to produce a fragment of 481 base pairs (bp).

This fragment is then inserted in the plasmid pCR2 (plasmid present in the Topo TA cloning kit, InVitrogen, Cat #K4550-40). The plasmid thus obtained has a size of 4432 bp and is designated pBP476.

All these operations are repeated twice more to obtain three "populations" of plasmids pBP476. The inserts of these plasmids are then sequenced. The consensus sequence (SEQ ID NO: 1), established on the basis of these three "populations" of plasmids pBP476 has a size of 462 bp and encoded a protein of 153 amino acids (SEQ ID NO: 2). This protein is cats' IGF-1 factor (=feline IGF-1).

Example 3

Construction of the Plasmid pBP477

The plasmid pBP476 (example 2) was digested by BamHl and Sall and the BamHl-Sall fragment of 468 bp thus obtained was ligated with the plasmid pVR1012 (FIG. 1 and example 7 of WO-A-98/03199; Hartikka J. et al, Human Gene Therapy, 1996, 7, 1205-1217), previously digested with BamHl and Sall to give the plasmid pBP477 (5334 bp). Under the control of the early promoter of the human cytomegalovirus or hCMV-IE (human Cytomegalovirus Immediate Early), this plasmid contains an insert encoding feline IGF-1.

Example 4

In vitro Biological Activity of the Product of the Feline IGF-1 Gene

CHO-K1 cells (ovarian hamster cells, available from the American Type Culture Collection under access No. CCL-61) are cultured in minimum essential medium or MEM (Gibco-BRL) in 60 mm diameter Petri dishes and are transfected with 5 µg of plasmid pBP477 (example 3), previously complexed with 10 µl of LipofectAmine PLUS® (Cat #10964-013, Gibco-BRL, Cleveland, Ohio, USA). The conditions of formation of the complexes DNA/LipofectAmine® and of transfection of the cells are those recommended by the supplier (Gibco-BRL). 48 hours after transfection, the supernatants of the cultures are collected and frozen.

Some CRFK cells are cultured in plates comprising 96 wells at a rate of 100,000 cells per well in MEM medium containing an addition of 0.1% of BSA and 1% of foetal calf serum. 24 hours later, the culture medium is removed and then diluted or undiluted culture supernatant of the CHO-K1 cells transfected with the plasmid pBP477 is added to the cultures. Each dilution of the supernatant (1/1, 1/5, 1/10 and 1/100) is tested in triplicate in MEM medium. The negative control consists of a CHO-K1 culture supernatant without serum and without transfection with pBP477. After 24 hours of culture, the CRFK cells are incubated at 37° C. in the presence of tritiated thymidine for the last 8 hours of culture (final tritiated thymidine concentration: 2.5 µCi/ml). The culture plates are stored at −20° C. The radioactivity is measured by reading using a MicroBeta trilux counter (Wallac).

The supernatants of CHO-K1 cells transfected with the plasmid pBP477 gave the following results:

| Supernatant dilution | Number of wells | Average radioactivity | Standard deviation | Proliferation index |
|---|---|---|---|---|
| Negative control | 3 | 2123 | 327 | 0% |
| 1/100 | 3 | 2872 | 657 | 135% |
| 1/10 | 3 | 8444 | 646 | 397% |
| 1/5 | 3 | 8990 | 912 | 423% |
| 1/1 | 3 | 9533 | 1091 | 449% |

The results of each test are expressed by their proliferation index corresponding to the ratio of the average radioactivity values for the sample and the negative control expressed as a percentage.

These results show that the product of the feline IGF-1 gene expressed by the plasmid pBP477 has biological activity on in vitro cells.

Example 5

Culture of the FIV Virus

Feline immunodeficiency viruses of the Villefranche IFFA 1/88 strain (Steffan A. M. et al., J. Gen. Virol., 1994, 75, 3647-3653) or Petaluma strain are cultivated on auxiliary feline T lymphocyte cells (for example Q201; Willet B. et al., J. Gen. Virol., 1997, 78, 611-618), for the amplification thereof.

The Q201 cells are cultured in Falcon 25 cm² with Eagle-MEM medium supplemented by 2 mM of glutamine, 10% of calf serum, 100 Ul/ml of penicillin, 100 µg/ml of streptomycin and 100 Ul/ml of recombinant human 2-interleukin containing about 100,000 cells per ml. The cells are cultivated at +37° C.

After 3 days, the cell layer is confluent. The culture medium is then replaced and the FIV virus is added in a proportion of 5 pfu/cell.

When the cytopathogenic effect (CPE) is complete (generally 48 to 72 hours after the beginning of culturing), the viral suspensions are collected then clarified by centrifugation and frozen at −80° C. 3 to 4 successive passages are generally required for the production of a viral batch. The viral batch is stored at −80° C.

Example 6

Extraction of Viral RNA from FIV

The viral RNA contained in 100 ml of viral suspension of the FIV Villefranche strain is extracted after thawing with solutions from the High Pure™ Viral RNA Kit (Cat #858 882, Roche Molecular Biochemicals), following the supplier's instructions for the extraction stages. The RNA sediment obtained at the end of extraction is resuspended with 1 to 2 ml of sterile distilled water without RNase.

Example 7

Construction of the Plasmid pBP371

The complementary DNA (cDNA) of FIV is synthesized with the Gene Amp RNA PCR Kit (Cat #N 808 0017, Perkin-Elmer, Norwalk, Conn. 06859, USA), using the conditions provided by the supplier.

A reverse transcription reaction followed by a polymerase chain reaction (RT-PCR) is carried out using 50 µl of the viral RNA suspension of FIV (example 6) and the following oligonucleotides:

```
FC116 (36 mer)
                                    (SEQ ID NO:6)
5'TTTTTTCTGCAGCAATAAGAATGGCAGAAGGATTTG3' and FC117 (36 mer)
                                    (SEQ ID NO:7)
5'TCGCACCTGAAACATCTCGAGTGTTTCCACATGTAT3'
```

This pair of oligonucleotides allows the incorporation of a PstI restriction site, a XhoI restriction site and an ATG initiation codon at 5' of the insert.

The synthesis of the first cDNA strand takes place by elongation of the oligonucleotide FC117 after hybridization of the latter with the RNA matrix.

The synthesis conditions of the first cDNA strand are a temperature of 42° C. for 15 min, then 99° C. for 5 min and finally 4° C. for 5 min. The conditions of the PCR reaction in the presence of the pair of oligonucleotides FC116 and FC117 are a temperature of 95° C. for 2 min, then 40 cycles (95° C. for 30 sec, then 50° C. for 45 sec and 72° C. for 3 min) and finally 72° C. for 7 min to produce a fragment of 1476 bp.

This fragment is digested by the PstI restriction enzyme then by the XhoI restriction enzyme to isolate the PstI-XhoI fragment of about 1450 bp after electrophoresis in agarose gel. This fragment is called fragment A.

A second reverse transcription reaction followed by a polymerase chain reaction (RT-PCR reaction) is carried out with 50 µl of the viral RNA suspension of FIV (example 6) and with the following oligonucleotides:

FC118 (36 mer)
(SEQ ID NO:8)
5'ATACATGTGGAAACACTCGAGATGTTTCAGGTGCGA3' and

FC119 (54 mer)
(SEQ ID NO:9)
5'TTTTTTGGATCCCCCGGGCTGCAGGAATTCTGAGATACTTCATCATTCCTCCTC3'

This pair of oligonucleotides allows the incorporation of a XhoI restriction site, a BamHI restriction site and a stop codon at 3' of the insert.

The synthesis of the first cDNA strand takes place by elongation of the oligonucleotide FC118, after hybridization of the latter with the RNA matrix.

The synthesis conditions of the first cDNA strand are a temperature of 42° C. for 15 min, then 99° C. for 5 min and finally 4° C. for 5 min. The conditions of the PCR reaction in the presence of the pair of oligonucleotides FC118 and FC119 are a temperature of 95° C. for 2 min, then 40 cycles (95° C. for 130 sec, then 50° C. for 45 sec, and 72° C. for 3 min) and finally 72° C. for 7 min to produce a fragment of 1193 bp.

This fragment is digested by the XhoI restriction enzyme then by the BamHI restriction enzyme to isolate the XhoI-BamHI fragment of about 1170 bp, after electrophoresis in agarose gel. This fragment is called fragment B.

Fragments A and B are ligated with the eukaryotic expression plasmid pVR1012, previously digested by XbaI and EcoRI, to give the plasmid pBP371 (7467 bp). This plasmid contains, under the control of the early promoter of the human cytomegalovirus or hCMV-IE (human Cytomegalovirus Immediate Early), an insert encoding the env protein of FIV.

Example 8

Construction of the Plasmid pBP374

The complementary DNA (cDNA) of FIV is synthesized using the Gene Amp RNA PCR Kit (Cat #N 808 0017, Perkin-Elmer, Norwalk, Conn. 06859, USA), using the conditions provided by the supplier.

A reverse transcription reaction followed by a polymerase chain reaction (RT-PCR reaction) is carried out with 50 µl of the viral RNA suspension of FIV (example 6) and with the following oligonucleotides:

BP670 (37 mer)
(SEQ ID NO:10)
5'TTTGTCGACAAGGTAGGAGAGATTCTACAGCAACATG3' and

BP674 (40 mer)
(SEQ ID NO:11)
5'TTTGCGGCCGCGTTATTGAGCCATTACTAACCTAATATTG3'

This pair of oligonucleotides allows the incorporation of a SalI restriction site, a NotI restriction site, an ATG initiation codon at 5' and a stop codon at 3' of the insert.

The synthesis of the first cDNA strand takes place by elongation of the oligonucleotide BP674, after hybridization of the latter with the RNA matrix.

The synthesis conditions of the first cDNA strand are a temperature of 42° C. for 15 min, then 99° C. for 5 min and finally 4° C. for 5 min. The conditions of the PCR reaction in the presence of the pair of oligonucleotides BP670 and BP674 are a temperature of 95° C. for 2 min, then 40 cycles (95° C. for 30 sec, then 50° C. for 45 sec, and 72° C. for 3 min) and finally 72° C. for 7 min to produce a fragment of 1758 bp.

This fragment is digested by the SalI restriction enzyme then by the NotI restriction enzyme to isolate the SalI-NotI fragment of about 1750 bp, after electrophoresis in agarose gel. This fragment is ligated with the expression plasmid pVR1012, previously digested by SalI and NotI, to give the plasmid pBP374 (6633 bp). This plasmid contains, under the control of the early promoter hCMV-IE, an insert encoding the gag/pro proteins of FIV.

Example 9

Construction of the Plasmid pBP375

The complementary DNA (cDNA) of FIV is synthesized using the Gene Amp RNA PCR Kit (Cat #N 808 0017, Perkin-Elmer, Norwalk, Conn. 06859, USA), using the conditions provided by the supplier.

A reverse transcription reaction followed by a polymerase chain reaction (RT-PCR reaction) is carried out with 50 µl of the viral RNA suspension of FIV (example 6) and with the following oligonucleotides:

FC116 (36 mer)
(SEQ ID NO:6)
5'TTTTTTCTGCAGCAATAAGAATGGCAGAAGGATTTG3' and

FC120 (48 mer)
(SEQ ID NO:12)
5'TTTTTACCTGCATTTCCTTCTTCCAGTTTTACCTCTTGAATTTCGTTC3'

This pair of oligonucleotides allows the incorporation of a PstI restriction site, a BspMI restriction site and an ATG initiation codon at 5' of the insert.

The synthesis of the first cDNA strand takes place by elongation of the oligonucleotide FC120, after hybridization of the latter with the RNA matrix.

The synthesis conditions of the first cDNA strand are a temperature of 42° C. for 15 min, then 99° C. for 5 min and finally 4° C. for 5 min. The conditions of the PCR reaction in the presence of the pair of oligonucleotides FC116 and FC120 are a temperature of 95° C. for 2 min, then 40 cycles (95° C. for 30 sec, then 50° C. for 45 sec, and 72° C. for 3 min) and finally 72° C. for 7 min to produce a fragment of 265 bp.

This fragment is digested by the restriction enzyme PstI then by the restriction enzyme BspMI to isolate the PstI-BspMI fragment of about 240 bp, after electrophoresis in agarose gel. This fragment is called fragment C.

A second reverse transcription reaction followed by a polymerase chain reaction (RT-PCR reaction) is carried out with 50 µl of the viral RNA suspension of FIV (example 6) and with the following oligonucleotides:

```
BP672 (48 mer)
                                        (SEQ ID NO:13)
5'TTTACTGGAAGAAGGAAATGCAGGTAAAAGGAAAAGACAAAGAAGAA
G3' and BP673 (36 mer)
                                        (SEQ ID NO:14)
5'TTTAGATCTTTAGTCCATAAGCATTCTTTCTATTTC3'.
```

This pair of oligonucleotides allows the incorporation of a restriction site BspMI, a restriction site BglII and a stop codon at 3' of the insert.

The synthesis of the first cDNA strand takes place by elongation of the oligonucleotide BP673, after hybridization of the latter with the RNA matrix.

The synthesis conditions of the first cDNA strand are a temperature of 42° C. for 15 min, then 99° C. for 5 min and finally 4° C. for 5 min. The conditions of the PCR reaction in the presence of the pair of oligonucleotides BP672 and BP673 are a temperature of 95° C. for 2 min, then 40 cycles (95° C. for 30 sec, then 50° C. for 45 sec, and 72° C. for 3 min) and finally 72° C. for 7 min to produce a fragment of 246 bp.

This fragment is digested by the restriction enzyme BspMI then by the restriction enzyme BglII to isolate the BspMI-BglII fragment of about 230 bp, after electrophoresis in agarose gel. This fragment is called fragment D.

Fragments C and D are ligated with the expression plasmid pVR1012 previously digested by the restriction enzymes PstI and BglII to give the plasmid pBP375 (5316 bp). Under the control of the early promoter hCMV-IE, this plasmid contains an insert encoding the rev protein of FIV.

Example 10

Construction of the Plasmid pBP383

The complementary DNA (cDNA) of FIV is synthesized using the Gene Amp RNA PCR Kit (Cat #N 808 0017, Perkin-Elmer, Norwalk, Conn. 06859, USA), using the conditions provided by the supplier.

A reverse transcription reaction followed by a polymerase chain reaction (RT-PCR reaction) is carried out with 50 µl of the viral RNA suspension of FIV (example 6) and with the following oligonucleotides:

```
BP680 (29 mer)
                                        (SEQ ID NO:15)
5'TTTCTGCAGATGGAAGACATAATAGTATT3' and BP681 (32 mer)
                                        (SEQ ID NO:16)
5'TTTAGATCTCTAAGCAGTAGTTATTGATAATG3'.
```

This pair of oligonucleotides allows the incorporation of a BglII restriction site, a PstI restriction site, an initiation ATG codon at 5' and a stop codon at 3' for the insert.

The synthesis of the first cDNA strand takes place by elongation of the oligonucleotide BP681, after hybridization of the latter with the RNA matrix.

The synthesis conditions of the first cDNA strand are a temperature of 42° C. for 15 min, then 99° C. for 5 min and finally 4° C. for 5 min. The conditions of the PCR reaction in the presence of the pair of oligonucleotides BP680 and BP681 are a temperature of 95° C. for 2 min, then 40 cycles (95° C. for 30 sec, then 50° C. for 45 sec, and 72° C. for 1 min) and finally 72° C. for 7 min to produce a fragment of 254 bp.

This fragment is digested by the PstI restriction enzyme then by the BglII restriction enzyme to isolate the PstI-BglII fragment of about 240 bp, after electrophoresis in agarose gel. This fragment is ligated with the expression plasmid pVR1012, previously digested by PstI and BglII, to give the plasmid pBP383 (5089 bp). This plasmid contains, under the control of the early promoter hCMV-IE, an insert encoding the tat protein of FIV.

Example 11

Extraction of Viral RNA from FeLV

Type A FeLV viruses (Glasgow-1 strain) (Steward M. et al., J. Virol., 1986, 58, 825-834) were purified by techniques well known to a person skilled in the art. The genomic viral RNA of each virus was then isolated using the guanidium thiocyanate/phenolchloroform extraction technique described by P. Chomczynski and N. Sacchi (Anal. Biochem., 1987, 162, 156-159).

Example 12

Construction of the Plasmid pBP179

The complementary DNA (cDNA) of FeLV was synthesized using the Gene Amp RNA PCR Kit (Cat #N 808 0017, Perkin-Elmer, Norwalk, Conn. 06859, USA), using the conditions provided by the supplier.

A reverse transcription reaction followed by a polymerase chain reaction (RT-PCR reaction) is carried out with 50 µl of the viral RNA suspension of FeLV (example 11) and with the following oligonucleotides:

```
BP247 (29 mer)
                                        (SEQ ID NO:17)
5'TTTGTCGACCATGGAAAGTCCAACGCACC3' and BP249 (28 mer)
                                        (SEQ ID NO:18)
5'TTTGGATCCTCATGGTCGGTCCGGATCG3'
```

This pair of oligonucleotides allows the incorporation of a SalI restriction site, a BamHI restriction site, an ATG initiation codon at 5' and a stop codon at 3' of the insert.

The synthesis of the first cDNA strand takes place by elongation of the oligonucleotide BP249, after hybridization of the latter with the RNA matrix.

The synthesis conditions of the first cDNA strand are a temperature of 42° C. for 15 min, then 99° C. for 5 min and finally 4° C. for 5 min. The conditions of the PCR reaction in the presence of the pair of oligonucleotides BP247 and BP249 are a temperature of 95° C. for 2 min, then 40 cycles (95° C. for 30 sec, then 50° C. for 45 sec, and 72° C. for 1 min) and finally 72° C. for 7 min to produce a fragment of 1947 bp.

This fragment is digested by the SalI restriction enzyme then by the BamHI restriction enzyme to isolate the SalI-BamHI fragment of about 1935 bp, after electrophoresis in agarose gel. This fragment is ligated with the expression plasmid pVR1012, previously digested by SalI and BamHI, to give the plasmid pBP179 (6804 bp). This plasmid contains, under the control of the early promoter hCMV-IE, an insert encoding the env proteins of FeLV-A.

Example 13

Construction of the Plasmid pBP181

The complementary DNA (cDNA) of FeLV was synthesized using the Gene Amp RNA PCR Kit (Cat #N 808 0017, Perkin-Elmer, Norwalk, Conn. 06859, USA), using the conditions provided by the supplier.

A reverse transcription reaction followed by a polymerase chain reaction (RT-PCR reaction) was carried out with 50 µl of the viral RNA suspension of FeLV (example 11) and with the following oligonucleotides:

```
BP283 (33 mer)
                                       (SEQ ID NO:19)
5'TTGTCGACATGTCTGGAGCCTCTAGTGGGACAG3' and BP284 (40 mer)
                                       (SEQ ID NO:20)
5'TTGGATCCTTATTTAATTACTGCAGTTCCAAGGAACTCTC3'
```

This pair of oligonucleotides allows the incorporation of a SalI restriction site, a BamHI restriction site, an ATG initiation codon at 5' and a stop codon at 3' of the insert.

The synthesis of the first cDNA strand takes place by elongation of the oligonucleotide BP284, after hybridization of the latter with the RNA matrix.

The synthesis conditions of the first cDNA strand are a temperature of 42° C. for 15 min, then 99° C. for 5 min and finally 4° C. for 5 min. The conditions of the PCR reaction in the presence of the pair of oligonucleotides BP283 and BP284 are a temperature of 95° C. for 2 min, then 40 cycles (95° C. for 30 sec, then 50° C. for 45 sec, and 72° C. for 1 min) and finally 72° C. for 7 min to produce a fragment of 3049 bp.

This fragment is digested by the SalI restriction enzyme then by the BamHI restriction enzyme to isolate the SalI-BamHI fragment of about 3039 bp, after electrophoresis in agarose gel. This fragment is ligated with the expression plasmid pVR1012, previously digested by SalI and BamHI, to give the plasmid pBP181 (7908 bp). This plasmid contains, under the control of the early promoter hCMV-IE, an insert encoding the gag/pro proteins of FeLV-A.

Example 14

Preparation of the Plasmids

Any method of obtaining a suspension of purified plasmids may be used to prepare plasmids for the vaccination of cats. These methods are well known to a person skilled in the art. The plasmids are produced by culture of *Escherichia coli* K12 bacteria transformed by plasmids according to the invention. These include, in particular, the technique of alkaline lysis followed by two successive ultracentrifugation treatments over a gradient of chloride and caesium in the presence of ethidium bromide as described in Sambrook J. et al., (Molecular Cloning: A Laboratory Manual, 2nd Edition, Cold Spring Harbor Laboratory, Cold Spring Harbor, N.Y. 1989). Reference may also be made to the patent applications WO-A-95/21250 and WO-A-96/02658 which describe methods of producing plasmids suitable for vaccination on an industrial scale. For the requirements of vaccine production, the plasmids are resuspended so as to provide high-concentration solutions (>2 mg/ml) compatible with storage. For this purpose, the plasmids are resuspended either in ultrapure water or in a TE buffer (Tris-HCl 10 mM; EDTA 1 mM; pH 8.0).

Example 15

Production of Vaccines and Administration

The store of plasmid pBP477 is diluted in TE buffer, in physiological water or in BPS buffer and mixed with various immunogen-expressing vaccinal plasmids, in particular pBP371 (example 7) and/or pBP374 (example 8) and/or pBP375 (example 9) and/or pBP383 (example 10) and/or pBP179 (example 12) and/or pBP181 (example 13). These plasmids may also be, for example, those mentioned in the examples of WO-A-98/03660 and WO-A-00/77043.

The various mixtures of "immunogenic" plasmids and of the plasmid pBP477 thus obtained are co-administered intramuscularly to each cat. In this case, the doses of vaccine are injected in a volume of 1 ml.

Example 16

Formulation of the Plasmids

The mixture of "immunogenic" plasmids and the plasmid pBP477 (example 15) is diluted in TE buffer, physiological water or BPS buffer so as to obtain a concentration of 1 mg/ml. A solution of DMRIE-DOPE at 0.75 mM is prepared by take-up of a lyophilisate of DMRIE-DOPE with a suitable volume of sterile $H_2O$.

The formation of plamidic DNA-lipid complexes takes place by dilution of the solution of DMRIE-DOPE 0.75 mM in the solution of DNA at 1 mg/ml in equal proportions. The DNA solution is introduced gradually using a crimped needle 26G along the wall of the flask containing the cationic lipid solution so as to prevent foaming. The two solutions are stirred gently after being mixed. A composition containing 0.375 mM of DMRIE-DOPE and 500 µg/ml of DNA is finally obtained.

It is desirable that all the solutions used are at ambient temperature for all the above-described operations. DNA/DMRIE-DOPE complexing is allowed to take place at ambient temperature for 30 minutes before proceeding to immunization of the animals, as described in example 15.

Example 17

Construction of the Plasmid pCD018

The complementary DNA (cDNA) of FIV is synthesized with the Gene Amp RNA PCR Kit (Cat #N 808 0017, Perkin-Elmer, Norwalk, Conn. 06859, USA), using the conditions provided by the supplier.

A reverse transcription reaction followed by a polymerase chain reaction (RT-PCR) is carried out using 50 µl of the viral RNA suspension of FIV (example 6) and the following oligonucleotides:

FC118 (36 mer) (SEQ ID NO: 8) and

FC119 (54 mer) (SEQ ID NO: 9).

This pair of oligonucleotides allows the incorporation of a XhoI restriction site, a EcoRI restriction site and a stop codon at 3' of the insert.

The synthesis of the first cDNA strand takes place by elongation of the oligonucleotide FC118, after hybridization of the latter with the RNA matrix.

The synthesis conditions of the first cDNA strand are a temperature of 42° C. for 15 min, then 99° C. for 5 min and finally 4° C. for 5 min. The conditions of the PCR reaction in the presence of the pair of oligonucleotides FC118 and FC119 are a temperature of 95° C. for 2 min, then 40 cycles (95° C. for 130 sec, then 50° C. for 45 sec, and 72° C. for 3 min) and finally 72° C. for 7 min to produce a fragment of 1193 bp.

This fragment is digested by the XhoI restriction enzyme then by the EcoRI restriction enzyme to isolate the XhoI-EcoRI fragment of about 1150 bp, after electrophoresis in agarose gel. This fragment is called fragment E.

The pCMVβ plasmid (CLONTECH Laboratories Inc., Palo Alto, Calif., USA, Cat. Number#6177-1) is digested by the NotI restriction enzyme then by the EcoRV restriction enzyme to isolate the NotI-EcoRV fragment of 3689 bp, after electrophoresis in agarose gel. This fragment is called fragment F.

Fragments A (example 7), E and F are ligated together to give the plasmid pCD018 (6355 bp). This plasmid contains, under the control of the early promoter of the human cytomegalovirus or hCMV-IE (human Cytomegalovirus Immediate Early), an insert encoding the env protein of FIV.

Example 18

Vaccination of Cats

Three groups of Hill Grove SPF cats (specific pathogen-free), about 9 to 11 weeks old, were used in the experiment:

In the control group, 6 cats were injected by intramuscular (IM) route on day 0, day 28 and day 56 with 1.0 ml of physiological solution (NaCl 0.9% in water) containing 0.4 mg of a control plasmid coding for the equine herpesvirus type 1 (EHV-1) glycoprotein C (gC), In the second group, 6 cats were injected by intramuscular route on day 0, day 28 and day 56 with 1.0 ml of physiological solution containing 0.1 mg of plasmid pCD018 (example 17), 0.1 mg of plasmid pPB374 (example 8), 0.1 mg of plasmid pPB383 (example 10) and 0.1 mg of a plasmid coding for EHV-1 gC (in order to have the same quantity of injected plasmid), In the last group, 6 cats were injected by intramuscular route on day 0, day 28 and day 56 with 1.0 ml of physiological solution containing 0.1 mg of plasmid pCD018 (example 17), 0.1 mg of plasmid pPB374 (example 8), 0.1 mg of plasmid pPB383 (example 10) and 0.1 mg of plasmid pPB477 (example 3).

The three groups were then challenged on day 84 by intramuscular injection in the lumbar muscle of 1.0 ml containing 3.0 log10 CCID50 of FIV strain Petaluma (Pedersen et al., Vet Immunol Immunopathol 1989, 21(1), 111-29).

After vaccination and after challenge, blood and tissue samples are regularly taken in order to follow the evolution of viral infection, notably to follow the population of CD4 and CD8 lymphocytes, the quantity of FIV proviruses (by PCR) and the quantity of FIV viruses (by RT-PCR).

It should be understood that the invention defined by the attached claims is not limited to the particular embodiments mentioned in the foregoing description but includes variants which do not emerge from the scope or the spirit of the present invention.

---

I claim:

1. An isolated polynucleotide comprising the nucleotide sequence of SEQ ID NO: 1 or its full length complementary strand.

2. An isolated polynucleotide encoding a polypeptide having the amino acid sequence of SEQ ID NO: 2 or 3.

3. An isolated polynucleotide comprising a sequence which differs from the sequence SEQ ID NO: 1 due to the replacement of T by U, wherein the polynucleotide is an RNA sequence.

4. An expression vector comprising the polynucleotide according to claim 1 operably linked to a regulatory element or regulatory elements for in vitro or in vivo expression of the polynucleotide.

5. An expression vector comprising the polynucleotide according to claim 2 operably linked to a regulatory element or regulatory elements for in vitro or in vivo expression of the polynucleotide.

6. An immunizing composition against a feline disease, comprising at least one immunogen obtained from a feline pathogen or at least one vector expressing in vivo said immunogen, and an in vivo expression vector comprising a polynucleotide encoding a polypeptide having an IGF-1 activity selected from the group consisting of:

(i) a polynucleotide comprising the nucleotide sequence of SEQ ID NO: 1 or its full length complementary strand (ii) a polynucleotide encoding a polypeptide having the amino acid sequence of SEQ ID NO: 2;

(iii) a polynucleotide encoding a polypeptide having the amino acid sequence of SEQ ID NO:3;

and a veterinarily acceptable vehicle or excipient.

7. The immunizing composition according to claim 6, wherein the polynucleotide comprises the nucleotide sequence of SEQ ID NO: 1.

8. The immunizing composition according to claim 6, wherein the polynucleotide encodes a polypeptide having the amino acid sequence of SEQ ID NO: 2 or 3.

9. The immunizing composition according to claim 6, wherein the in vivo vector expressing said immunogen is a plasmid.

10. The immunizing composition according to claim 6, wherein the expression vector comprising the polynucleotide is a plasmid.

11. The immunizing composition according to claim 6, wherein said immunogen comprises an FIV immunogen.

12. The immunizing composition according to claim 6, wherein said immunogen comprises an FeLV immunogen.

13. The immunizing composition according to claim 6, wherein said immunogen comprises an FIV and an FeLV immunogen.

14. The immunizing composition according to claim 6, wherein said immunogen is selected from the group consisting of an FPV immunogen, an FIPV immunogen, an FHV immunogen, an FCV immunogen, a rabies virus immunogen, and a *Chlamydia* immunogen.

15. The immunizing composition according to claim 6, wherein the vector expressing in vivo said immunogen is a viral vector.

16. The immunizing composition according to claim 6, wherein the expression vector comprising the polynucleotide is a viral vector.

17. The immunizing composition according to claim 6, wherein said immunogen is selected from the group consisting of an inactivated immunogen, a live attenuated immunogen and a sub-unit or sub-units.

18. An isolated polynucleotide comprising a sequence encoding a polypeptide having the amino acid sequence of SEQ ID NO: 2 or 3.

19. A vector comprising the polynucleotide according to claim 1.

20. A vector comprising the polynucleotide according to claim 2.

21. An isolated polynucleotide encoding a polypeptide having an IGF-1 activity comprising a polynucleotide selected from the group consisting of:
 (i) a polynucleotide comprising the nucleotide sequence of SEQ ID NO: 1 or its full length complementary strand
 (ii) a polynucleotide encoding a polypeptide having the amino acid sequence of SEQ ID NO: 2 or 3
 (iii) a polynucleotide comprising a sequence which differs from the sequence SEQ ID NO: 1 due to the replacement of T by U, wherein the polynucleotide is an RNA sequence,
 (iv) a polynucleotide that differs from (i) or (ii) due to the degeneracy of the genetic code.

22. A vector that comprises the polynucleotide of claim 21.

* * * * *